United States Patent
Poojari et al.

(10) Patent No.: US 10,888,551 B2
(45) Date of Patent: Jan. 12, 2021

(54) DRUG DELIVERY SYSTEM

(71) Applicant: Indian Institute of Technology, Bombay, Mumbai (IN)

(72) Inventors: Radhika Poojari, Mumbai (IN); Dulal Panda, Mumbai (IN); Rohit Srivastava, Mumbai (IN)

(73) Assignee: INDIAN INSTITUTE OF TECHNOLOGY, BOMBAY, Mumbai (IN)

(*) Notice: Subject to any disclaimer, the term of this patent is extended or adjusted under 35 U.S.C. 154(b) by 205 days.

(21) Appl. No.: 15/763,845

(22) PCT Filed: Feb. 23, 2017

(86) PCT No.: PCT/IN2017/000049
§ 371 (c)(1),
(2) Date: Mar. 28, 2018

(87) PCT Pub. No.: WO2017/145179
PCT Pub. Date: Aug. 31, 2017

(65) Prior Publication Data
US 2018/0344710 A1   Dec. 6, 2018

(30) Foreign Application Priority Data
Feb. 24, 2016   (IN) .............................. 201621006380

(51) Int. Cl.
*A61K 31/44*  (2006.01)
*A61K 9/51*  (2006.01)

(52) U.S. Cl.
CPC ............ *A61K 31/44* (2013.01); *A61K 9/5146* (2013.01); *A61K 9/5153* (2013.01); *A61K 9/5161* (2013.01); *A61K 9/5169* (2013.01)

(58) Field of Classification Search
CPC .... A61K 31/44; A61K 9/5146; A61K 9/5153; A61K 9/5161; A61K 9/5169
See application file for complete search history.

(56) References Cited

U.S. PATENT DOCUMENTS

| | | | | |
|---|---|---|---|---|
| 2007/0224244 A1* | 9/2007 | Weber | ...................... | A61L 27/34 424/426 |
| 2011/0229580 A1* | 9/2011 | Srivastava | ........... | A61K 9/1652 424/493 |
| 2014/0212503 A1* | 7/2014 | Lee | ...................... | A61K 9/0019 424/499 |
| 2016/0038612 A1* | 2/2016 | Hoge | ..................... | A61K 47/52 514/44 R |

FOREIGN PATENT DOCUMENTS

WO   2008130180 A1   10/2008
WO   2011129549 A2   10/2011

OTHER PUBLICATIONS

Xing Liu et al; Multilayer Microcapsules as Anti-Cancer Drug Delivery Vehicle: Deposition, Sustained Release, and in vitro Bioactivity, Macromol. Biosci. 2005.

(Continued)

*Primary Examiner* — Robert A Wax
*Assistant Examiner* — Quanglong N Truong
(74) *Attorney, Agent, or Firm* — Mark M. Friedman (57) ABSTRACT

The present invention provides for a drug delivery system for anti-cancer compound and method of preparation thereof.

9 Claims, 7 Drawing Sheets

(56) References Cited

OTHER PUBLICATIONS

Ramasamy T et al. Layer-by-layer assembly of liposomal nanoparticles with PEGylated polyelectrolytes enhances systemic delivery of multiple anticancer drugs. Acta Biomater (2014).
Thiruganesh Ramasamy et al; Chitosan-Based Polyelectrolyte Complexes as Potential Nanoparticulate Carriers: Physicochemical and Biological Characterization, Pharmaceutical Research, May 2014, vol. 31, Issue 5, pp. 1302-1314.
Frank Caruso et al; Nanoengineering of Inorganic and Hybrid Hollow Spheres by Colloidal Templating, Nov. 1998.

\* cited by examiner

DRUG DELIVERY SYSTEM

TECHNICAL FIELD

The present invention relates to a drug delivery system for anti-cancer compounds. The invention particularly relates to drug delivery system i.e. layer-by-layer nano-particulate template nucleus encapsulated anti-cancer compound and a method of preparing said drug delivery system thereof.

BACKGROUND AND PRIOR ART

Cancer, also known as a malignant tumour or malignant neoplasm, is a group of diseases involving abnormal cell growth with potential to invade or spread to other parts of the body. Cancer is often treated with some combination of radiation therapy, surgery, chemotherapy, and targeted therapy. In 2012 about 14.1 million new cases of cancer occurred globally. It caused about 8.2 million deaths which accounts for about 14.6% of all human deaths. The risk of cancer increases significantly with age and rates are increasing as more people live to an old age.

Oral cancer has emerged as one of the deadliest cancers with its incidence increasing with an alarming rate. The major causes of oral cancer include use of tobacco and alcohol and exposure to Human Papilloma Virus (HPV). Despite the advancement in diagnostic techniques and treatment modalities like surgery along with chemo-radiotherapy, the treatment of oral cancer is still a major challenge. Therefore, identifying new therapeutic modalities for oral cancer remains a priority. Small molecule inhibitors of tyrosine kinases (TKIs) such as sorafenib represent an attractive therapeutic strategy for cancer treatment. One example of such small molecule TKI is sorafenib which exhibits broad target selectivity which inhibits tumor cell proliferation via Raf/MEK/ERK pathway (MAP Kinase), angiogenesis and tumor microenvironment signaling (metastasis and invasion), and drug resistant cancers. It also inhibits c-Raf-1 and B-Raf proteins.

The therapeutic effects of sorafenib have been validated in a number of preclinical and clinical studies including advanced hepatocellular carcinoma, renal cancer, breast cancer, colon cancer, melanoma and non-small cell lung cancer. Recently, the combination of sorafenib and radiation has been found to produce synergistic effects in oral carcinoma.

Other small molecule tyrosine kinase inhibitors include dasatinib, erlotinib, gefitinib, imatinib, lapatinib, nilotinib and sunitinib. However, common drawbacks faced by these molecules includes instability, poor oral availability, inability to cross the blood-brain barrier, pH sensitivity, poor solubility, rapid metabolism and clearance, repeated high dose medication, adverse drug reactions such as gastro-intestinal bleeding, hypertension, hepatotoxicity, dermatological toxicity (hand-foot syndrome), dysgeusia and diarrhea severely limits the therapeutic effectiveness of sorafenib in cancer patients.

To counteract these drawbacks, research has been drawn towards electrostatic interactions which assist in efficient loading of small molecule inhibitors in the polyelectrolyte shell. A modification of the particle surface by coating with ionic polyelectrolyte(s) layers serves the purpose by rendering the small molecule inhibitors more effective in oral, intravenous, intratumoral or subcutaneous delivery therapeutic regimens. The surface chemistry retains the biological functionalities (proteins, enzymes, antigens, DNA and drugs) in an intact state and allows sustained release of the entrapped molecules form the system (S. De Koker et al, *Polymeric multilayer capsules for drug delivery, Chem. Soc. Rev.* 41 (2012) 2867-84 and G. B. Sukhorukov et al, *Porous calcium carbonate microparticles as templates for encapsulation of bioactive compounds, J. Mater. Chem.* 14 (2004) 2073-81). Earlier studies have reported calcium carbonate micro-particles using layer-by-layer assembly for the delivery of bioactive compounds {K. Radhakrishnan et al, *Biologically triggered exploding protein based microcapsules for drug delivery, Chem. Commun.* 48 (2012) 2307-9; Y Yan et al, *Toward therapeutic delivery with layer-by-layer engineered particles, ACS Nano* 5 (2011) 4252-7; *Release of Insulin from Calcium Carbonate Microspheres with and without layer-by-layer thin coatings'*, Katsuhiko et al, *Polymers*, 2014, 6, 2157-2165 and *Layer-by-layer self-assembled shells for drug delivery,'* Katsuhiko et al, *Advanced Drug Delivery Reviews, vol.* 63, Issue 9, 14 Aug. 2011, pages 762-771}. However, it has been observed that drug loaded microspheres are too large in diameter for intravenous administration. The large sized microspheres embolize easily in the blood vessels, trigger an opsonization effect in the immune system and have difficulty in crossing endothelial barriers in various hosts. Cellular internalization is also affected, which is a crucial factor depending on the particle size. Hence calcium carbonate nanoparticles were studied and reported for the sustained release of granulocyte colony-stimulating factor and betamethasone phosphate by Y. Ueno et al, *Drug-incorporating calcium carbonate nanoparticles for a new delivery system., J. Control. Release* 103 (2005) 93-8.

The technique of bilayering or layer-by-layer has been studied with polymeric multilayer dextran-sulfate/poly-L-arginine microcapsules as the vaccine-delivery vehicles in dendritic cells which displayed good toleration in mucosal tissue and induced potent cellular immune response {B. G. De Geest et al, *Polymeric multilayer capsule-mediated vaccination induces protective immunity against cancer and viral infection, ACS Nano.* 6 (2012) 2136-49}.

Another publication, '*Multilayer-coated liquid crystalline nanoparticles for effective sorafenib delivery to hepatocellular carcinoma* by R. K. Thapa et al, *ACS Appl. Mater. Interfaces,* 7(2015), 20360-20368' discloses layer-by-layer (LbL) polymer-assembled sorafenib loaded monolein based liquid crystalline nanoparticles with particle size of ~165 nm and polydispersity index of ~0.14. However, use of lipids (e.g. monolein) results in high production costs, drug leakage (drug expulsion) and fusion of encapsulated drug or molecules is seen. Other drawbacks of this teaching include short half-life, degradation, relatively high water content, and stability problem and require presence of suitable surfactants.

OBJECT OF THE INVENTION

It is therefore one of the primary objects of the invention is to provide for drug delivery system which can circumvent drawbacks associated with prior art techniques and increase the availability and targeting ability of anti-cancer compound in cancer therapy. It is another object of the present invention to provide for a drug delivery system which is cost effective and easy to manufacture. It is a further object of the present invention to provide for a method for manufacturing the drug delivery system of the present invention.

SUMMARY

The present invention provides for a drug delivery system for anti-cancer compounds and method of preparation thereof.

DETAILED DESCRIPTION OF DRAWINGS

The foregoing summary, as well as the following detailed description of the present invention will be better understood when read in conjunction with the appended drawings. For the purpose of assisting in the explanation of the invention, there are shown in the drawings embodiments which are presently preferred and considered illustrative. It should be understood, however, that the invention is not limited to the precise arrangements and instrumentalities shown therein. In the drawings:

FIG. 1 depicts (A) A schematic representation of sorafenib encapsulated in layer-by-layer assembled $CaCO_3$ nanoparticles termed as the LbL-nanosoraf (Sraf-CCPELbL NP); (B) Zeta-potential measurements of sequentially layered polyelectrolytes $CaCO_3$ nanoparticles with Sraf (Sraf-CCPELbL NP) and without Sraf (CCPELbL NP). 0 point indicates the surface charge at the core level. The surface charge of each layer represents the mean±SE (n=3);

FIG. 3 shows (A, C, E and G) Qualitative KB cell uptake analysis by CLSM and DIC (B, D, F and H) images of control cells, CCPELbL NP (100 µg/mL) and LbL-nanoRhB (RhB-CCPELbL NP, 100 µg/mL) treated cells at 3 hours and 24 hours. Scale bar: 50 µm. (I) Quantitative flow cytometric analysis showing the cellular uptake efficiency of LbL-nanoRhB (RhB-CCPELbL NP, 100 µg/mL) at 3 hours and 24 hours by KB cells. Data represent as the mean±SD (n=3). (J) DIC and (K) CLSM images showing intracellular distribution of FITC-CCPELbL NP (green) in KB cells at 24 hours incubation. Nuclei were stained red with propidium iodide. Scale bar: 50 µm. Ultrastructural TEM images of control KB cells (L), CCPELbL NP (100 µg/mL) (M) and LbL-nanosoraf (Sraf-CCPELbL NP) (100 µg/mL) (N and O) treated cells at 24 hours. Inset of FIG. O shows an enlarged image of LbL-nanosoraf (Sraf-CCPELbL NP) internalization by KB cells (arrow). Scale bar: 2 µm.

DETAILED DESCRIPTION OF THE INVENTION

For the purposes of the following detailed description, it is to be understood that the invention may assume various alternative variations and step sequences, except where expressly specified to the contrary. Moreover, other than in any operating examples, or where otherwise indicated, all numbers expressing, for example, quantities of ingredients used in the specification are to be understood as being modified in all instances by the term "about" in which "about" is defined as ±10% of the nominal value. It is noted that, unless otherwise stated, all percentages given in this specification and appended claims refer to percentages by weight of the total composition.

Thus, before describing the present invention in detail, it is to be understood that this invention is not limited to particularly exemplified process parameters that may of course, vary. It is also to be understood that the terminology used herein is for the purpose of describing particular embodiments of the invention only, and is not intended to limit the scope of the invention in any manner.

The use of examples anywhere in this specification including examples of any terms discussed herein is illustrative only, and in no way limits the scope of the invention or of any exemplified term. Likewise, the invention is not limited to various embodiments given in this specification.

Unless otherwise defined, all technical and scientific terms used herein have the same meaning as commonly understood by a person skilled in the art to which this invention pertains. In the case of conflict, the present document, including definitions will control.

It must be noted that, as used in this specification and the appended claims, the singular forms "a," "an" and "the" include plural referents unless the content clearly dictates otherwise. The terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention. As used herein, the terms "comprising", "including", "having", "containing", "involving" and the like are to be understood to be open-ended, i.e., to mean including but not limited to.

In one aspect, the present invention provides for a drug delivery system for anti-cancer compounds. The drug delivery system includes a template nucleus for encapsulation of anti-cancer compounds in which the template nucleus is in nano-particulate form. The template nucleus is selected form at least one of calcium carbonate, calcium phosphate, mesoporous silica. Preferably, calcium carbonate is used as a template nucleus. Calcium carbonate particles possess good properties such as a high specific surface area and high absorbability, benefits to form linkage at the interface of two materials to improve the mechanical properties of materials.

A biodegradable core template like calcium carbonate is necessary for strong electro-statistically binding of the polyelectrolytes. Calcium carbonate core template is of primary use for encapsulation, since it can be dissolved under mild conditions. Also calcium carbonate is a biocompatible, biodegradable, non-toxic, natural mineral which is cost effective easy to scale-up, FDA approved, used as calcium supplements for human use. Thereby these properties make it feasible for its use. Overall particle size of 100-300 nm±15 nm is optimal for cellular internalization and suitable for in vivo studies.

It is known that intravenously or subcutaneously administered nanoparticles get accumulated easily in tumor tissues and their plasma drug concentration is higher. Due to the enhanced permeability of tumor endothelium and lack of lymphatic drainage in tumor cells, there is increased extravasation and accumulation of drug in tumor vasculature and tumor tissue. However oral administration of drugs especially small molecule tyrosine kinase inhibitors face drawbacks such as instability, inability to cross the blood-brain barrier, rapid degradation, pH sensitivity and losing its biological potency. To counteract these drawbacks, electrostatic interactions of bilayers assist in efficient protection of sorafenib encapsulated in calcium carbonate nanoparticles. And a biodegradable core template like calcium carbonate is necessary for strong electrostatic binding of polyelectrolytes.

The anti-cancer compound is small molecule tyrosine kinase inhibitors selected from at least one of dasatinib, erlotinib, gefitinib, imatinib, lapatinib, nilotinib, sorafenib and sunitinib, regorafenib, dasatinib, vemurafenib, taxol class of taxanes, antineoplastic agents, their salts, solvates, analogs, polymorphs, derivatives, isomers, enantiomers thereof.

The drug delivery system further comprises of at least two polyelectrolytes for polymeric layering of encapsulated anti-cancer compound, said polyelectrolyte selected from at least one polyanionic and at least one polycationic electrolyte for forming at least two layers; one layer each of polyanionic electrolyte and polycationic electrolyte respectively and not necessarily in that order. The polyanionic electrolytes for polymeric layering are selected from at least one of dextran sulfate, polyethylene glycol, cellulose, protamine, and alginate. The polycationic electrolytes for polymeric layering are selected from at least one of poly-L-arginine, polyglycolic acid, poly-L-lysine, chitosan, protamine.

In one embodiment of the invention, the layering results in bilayers i.e. two layers each of polyanionic and polycationic polymers alternately such that no two consecutive layers are identical.

The drug delivery system of the present invention is a layer-by-layer nano-particulate template nucleus encapsulated anti-cancer compound.

A method of preparing of layer-by-layer nano-particulate template nucleus encapsulated anti-cancer compound for oral delivery comprising the steps of adding anti-cancer compound to 0.1M calcium chloride and mixing for ten minutes. Adding the resultant solution drop wise to 0.1M sodium carbonate solution under vigorous stirring at 2000 rpm for fifteen minutes. This is followed by coating resultant calcium carbonate nanoparticles by dispersing in 5 mL of polyanionic solution containing sodium chloride. The resultant nanoparticles are stirred in 5 mL of polycationic solution in 0.5M sodium chloride and layer-by-layer nano-particulate template encapsulated anti-cancer compound is incubated in ethylene diamine tetraacetic acid for dissolving the template nucleus. The pellet is washed carefully to remove the dissolved ions.

A critical process parameter is drop wise addition under vigorous agitation lead to the formation of nanoparticles of controlled size rather than an instant mixture of two or more ion sources at a gentle mixing rate. The reduction in the particle size with the increase in stirring velocity is due to the rapid nucleation process in the solutions allowing formation of huge number of small nuclei in this mixing interval.

A vigorous stirring speed of 2000 rpm leads to the formation of small-sized nanoparticles which is controlled. In contrast, the instant mixing of the two ion sources at a gentle mixing speed lead to the formation of large sized particles.

The interpenetrating network of polyelectrolytes within the interior and the polyeletrolyte membrane creates a diffusion barrier. The assembled layers onto the nanoparticles ensure protection of anti-cancer compound encapsulated in template nucleus nanoparticles.

The following examples are provided to better illustrate the claimed invention and are not to be interpreted in any way as limiting the scope of the invention. All specific materials, and methods described below, fall within the scope of the invention. These specific compositions, materials, and methods are not intended to limit the invention, but merely to illustrate specific embodiments falling within the scope of the invention. One skilled in the art may develop equivalent materials, and methods without the exercise of inventive capacity and without departing from the scope of the invention. It is the intention of the inventors that such variations are included within the scope of the invention.

EXAMPLE

Materials:

Sorafenib tosylate (Sraf) was provided by Cipla Ltd., India. Calcium chloride ($CaCl_2$), sodium carbonate ($Na_2CO_3$), dextran sulfate (10 kDa), poly-L-arginine HCl (70 kDa), rhodamine B (RhB), sulforhodamine B (SRhB) reagent, propidium iodide (PI), fluorescein isothiocyanate (FTIC) and phosphate buffered saline (PBS) pellets were purchased from Sigma-Aldrich, India. Ethylenediaminetetraacetic acid disodium salt (EDTA) and dimethyl sulfoxide (DMSO) were of analytical reagent grade. Human oral cancer KB cells were procured from National Centre for Cell Sciences (NCCS), Pune, India. Dulbecco's modified eagles medium (DMEM) supplemented with 10% fetal bovine serum (FBS) and 1% penicillin-streptomycin solution was procured from HiMedia, Mumbai, India and used as the cell culture medium. Cells were grown in humidified environment at 37° C. with 5% $CO_2$.

Figure 1A:
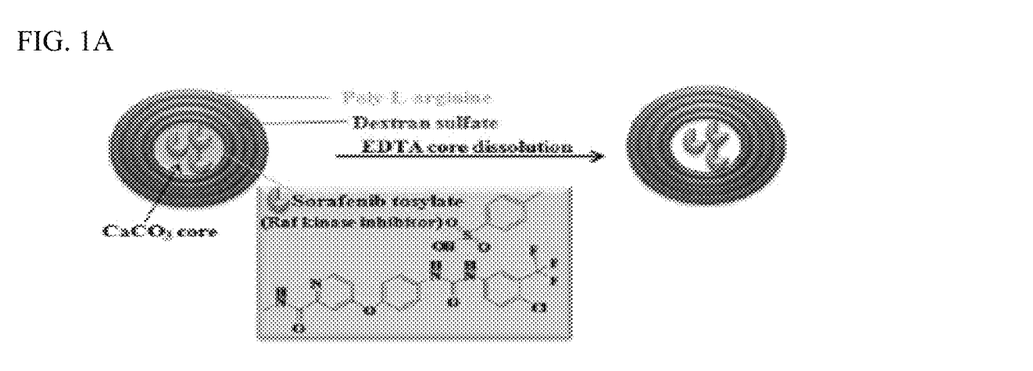

Preparation of LbL-Nanosoraf:

The layer-by-layer or LbL process is based on the physical adsorption, diffusion by pores and electrostatic mediated interactions. As seen in FIG. 1; the LbL-nanosoraf (Sraf-CCPELbL NP) was prepared using calcium carbonate as a biocompatible template nucleus. To encapsulate sorafenib tosylate, 200 μL of a 2 mg/mL stock solution of drug was added to 0.1M calcium chloride and mixed for ten minutes. This solution was then added drop-wise to 0.1M sodium carbonate solution under vigorous stirring at 2000 rpm for fifteen minutes. The calcium carbonate nanoparticles were washed with distilled water and subsequently coated by dispersing in 5 mL of polyanionic dextran sulfate solution (2 mg/2 mL) containing 0.5M sodium chloride. The nanoparticles were collected by centrifugation and the excess dextran sulfate was removed by washing two times with distilled water. The nanoparticles were stirred in 5 mL of polycationic poly-L-arginine solution (1 mg/mL) in 0.5M sodium chloride, centrifuged and washed with distilled water to remove excess poly-L-arginine.

The layering process was repeated till the polyelectrolytes dextran sulfate/poly-L-arginine was deposited forming two bilayers. Then the LbL nanoparticles were incubated with 0.2M EDTA solution (pH 5.2) for ten minutes for the calcium carbonate core dissolution, centrifuged and the pellet was washed carefully. The addition of EDTA lead to the dissolution of the core template resulting in the formation of sorafenib encapsulated nanoparticles with a protective bi-layered polyelectrolyte shell membrane (FIG. 1A). The washing steps were repeated three times to remove the dissolved ions. The nanoparticles were finally re-suspended in 1 mL of PBS (pH 7.4) and the concentration was determined by hemocytometry.

For comparative results, the bare CCPELbL NPs or calcium carbonate poly electrolyte layer-by-layer based nanoparticles were prepared similarly in the absence of sorafenib and characterized as follows—

Characterization—

1. Physico-chemical characterization of LbL-nanosoraf—
   a. Dynamic light scattering and zeta-potential analysis—The size and size distribution of bare CCPELbL NPs (1 mg/ml) and LbL-nanosoraf (Sraf-CCPELbL NPs) suspension (1 mg/mL) was measured by dynamic light scattering (DLS, 90 Plus, Brookhaven Instruments Corporation, USA). The surface charge of bare CCPELbL NPs and LbL-nanosoraf NPs was determined by ZetaPlus Zeta-Potential Analyzer (Brookhaven Instruments Corporation, USA) at room temperature in double deionised water. The zeta potential was determined at each adsorption step during the LbL synthesis procedure. The experiment was performed three times.

Figure 1B:
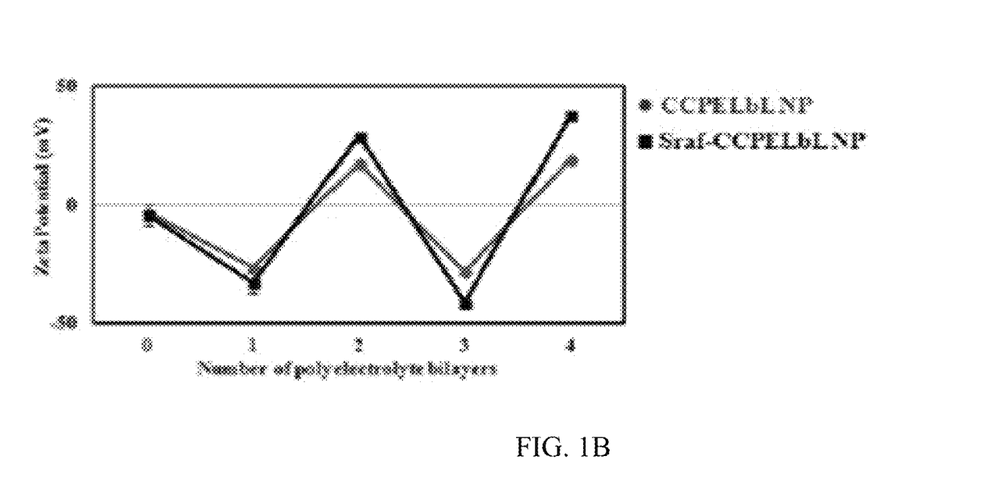

It was observed that the bare CCPELbL NP and LbL-nanosoraf exhibited a hydrodynamic diameter ranging from 100 to 300±15 nm as measured by DLS. A DLS measurement provides an average hydrodynamic radius of the particles. The particle size depicted in the SEM images was smaller than the average sizes obtained by DLS, which could be due to shrinkage of the particles during drying process for SEM imaging. Hence, the particle size obtained was considered suitable for cellular internalization and in vivo studies. The LbL self-assembly process after each adsorption was measured by zeta potential as shown in FIG. 1B. Calcium carbonate plus dextran sulfate (layer 1) exhibited a strong negative zeta potential indicating its successful coating on the calcium carbonate cores. The mean zeta potential of bare CCPELbL NP shows a sequential adsorption of polyanions at −26.41±1.19 mV to −27.96±1.66 mV and polycations at 17.42±1.72 mV to 18.92±1.90 mV. The LbL-nanosoraf exhibited a negative surface charge from dextran sulfate −37.78±4.40 mV to −41.44±1.30 mV, which alternated with the positive surface charge from poly-L-arginine 29.20±0.86 mV to 37.70±0.68 mV, indicating its LbL assembly confirmation (FIG. 1B). The mean polydispersity index (PDI) of Sraf-CC NP core was 0.30±0.035 whereas; LbL-nanosoraf was 0.005±0.001 indicating a well-dispersed formulation. The encapsulation efficiency of sorafenib in LbL-nanosoraf was found to be 61±4%.

b. Optical microscopy: A drop of LbL-nanosoraf suspension was placed on a glass slide and the number of particles was counted using a haemocytometer with the help of an Olympus light microscope. Optical microscopy depicted ~500×$10^6$ particles/mL using haemocytometric counts.

c. Field-emission gun scanning electron microscopy analysis: For field-emission gun scanning electron microscopy analysis (FEG-SEM), the dried Sraf-CC NP core and LbL-nanosoraf samples before and after core dissolution with EDTA were placed on a stub, and coated with gold using a sputter gold coater Auto Fine Coater (JEOL, Tokyo, Japan). The SEM images were captured using FEG-SEM (JSM-7600 F, Japan).

Figure 2:
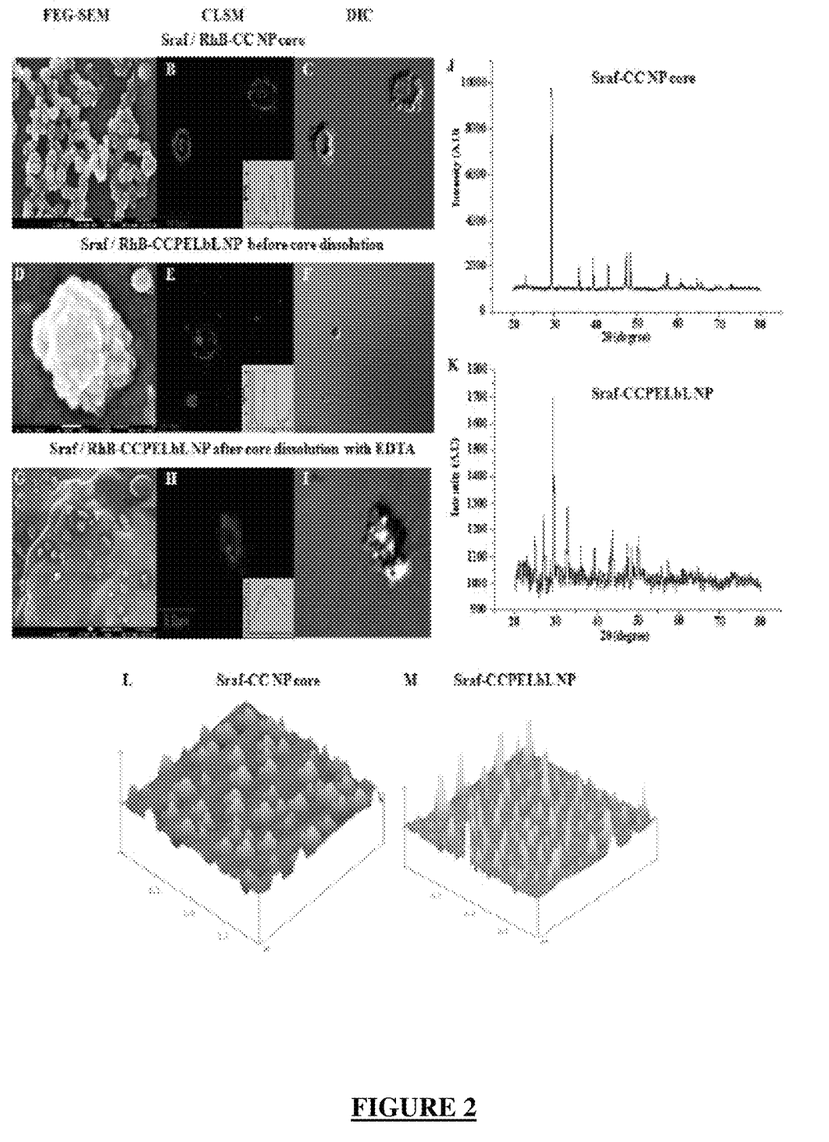
FIG. 2 illustrates physico-chemical characterization of LbL-nanosoraf (Sraf-CCPELbL NP). (A, D and G) Surface morphology of Sraf-CC NP core and LbL-nanosoraf (Sraf-CCPELbL NP) before and after core dissolution with EDTA by FEG-SEM. Scale bar: 100 nm. FEG-SEM insets showing enlarged images of individual NP. (B, E and H) CLSM and (C, F and I) DIC images of RhB-CC NP core and LbL-nanoRhB (RhB-CCPELbL NPs) before and after core dissolution with EDTA (Scale bars: 10 µm, 20 µm and 5 µm), and their respective CLSM insets showing line scan red fluorescence intensities. (J and K) Powder XRD patterns of Sraf-CCNP core and LbL-nanosoraf (Sraf-CCPELbL NP). (L and M) AFM surface topography 3D-images of Sraf-CC NP core and LbL-nanosoraf (Sraf-CCPELbL NP). Z scale is 25 nm/div.

It was observed that the surface of the core-shell particle LbL-nanosoraf before and after the core dissolution with EDTA was rougher than the Sraf-CC NP core (FIGS. 2A, D and G), which may be due to the adsorption of the rigid polyelectrolyte multilayers. The size of the nanoparticles was found to be in the range of 100-200±20 nm.

d. Confocal laser scanning microscopic analysis: A drop of RhB-CC NP core (RhB=Rhodamine B dye) and LbL-nanoRhB suspension before and after core dissolution with EDTA was placed on a cover glass-slip. Confocal images were taken using FV500 Confocal laser scanning microscope (CLSM, Olympus, Tokyo, Japan). The line scan fluorescence intensities of RhB were recorded.

The CLSM and DIC images of RhB-CC NP core and LbL-nanoRhB before core dissolution with EDTA depicted an intact core structure, intact electrostatically layered polyelectrolytes structure of nanoparticles prior, and a collapsed structure on core removal after EDTA treatment (FIGS. 2B, C, E, F, H and I). The line scans of RhB-CC NP core and LbL-nanoRhB NPs before and after dissolution with EDTA depicted the red fluorescence intensities of RhB in their respective images (Insets FIGS. 2B, E and H).

e. X-ray diffraction analysis: To analyze the degree of crystallinity, X-ray diffraction (XRD) identification of Sraf-CC NP core versus LbL-nanosoraf was performed by powder XRD using a Philips Powder diffractometer PW3040/60 with Cu Kα radiation ($\lambda$=1.54A°) at an accelerating voltage of 40 kV, current 30 mA, scanning rate 4°/min and 2θ range from 20° to 80°. The XRD profiles of Sraf-CC NP core revealed characteristic diffraction peaks at 2θ of 30°, 35°, 40°, 44°, 48° and 50° (FIG. 2J) whereas, LbL-nanosoraf showed peaks at 2θ of 24°, 27°, 30°, 34°, 40°, 44°, 48° and 50° (FIG. 2K).

f. Atomic force microscopic analysis: To analyze the surface topography, a drop of Sraf-CC NP core and LbL-nanosoraf suspensions were applied onto a freshly cleaved mica substrate followed by air drying. Atomic force microscopy (AFM) images of the dried samples were taken on a Nano-scope IIIa Multimode SFM (Digital Instruments Inc.) operating at a tapping mode at room temperature.

The AFM surface topography of Sraf-CC NP core revealed its smooth surface texture. The thickness of the polyelectrolyte multilayers in LbL-nanosoraf can be tuned by the LbL assembly technique, which provides a diffusion barrier for the encapsulated Sraf and revealed somewhat a rough texture (FIGS. 2L and M).

g. Encapsulation efficiency: The encapsulation efficiency of sorafenib in the LbL-nanosoraf was determined by an UV spectrophotometer (Perkin Elmer, Lambda 25) and calculated using a formula: Drug encapsulation efficiency %=(amount of loaded sorafenib/amount of sorafenib added)×100%. Each experiment was repeated three times. The encapsulation efficiency of sorafenib in LbL-nanoSraf was found to be 61±4%.

2. Cell Uptake Efficiency and Internalization:

a. CLSM and FACS analysis—For cellular uptake analysis, KB cells were seeded on glass cover-slips in 24 well plates (Nunc, USA) at $5\times10^4$ cells/well density. After reaching 70% confluency, the cells were incubated with LbL-nanoRhB NP (100 µg/mL) for 3 hours and 24 hours at 37° C. The untreated cells and bare CCPELbL NP (100 µg/mL) served as negative controls. Confocal images were acquired using FV500 Confocal Laser Scanning Microscopy i.e. CLSM (Olympus, Tokyo, Japan) equipped with a 63× oil immersion objective lens. The extent of intracellular uptake of the indicated nanoparticles were quantified using flow cytometer BD FACS ARIA special order system (Becton and Dickinson, USA) and the data were analyzed using the FCS Express Software. The intracellular distribution of FITC-CCPELbL NP (100 µg/mL) at 24 hours in KB cells was analyzed using CLSM. PI was used for the staining of DNA. Each experiment was performed three times.

Figure 3:
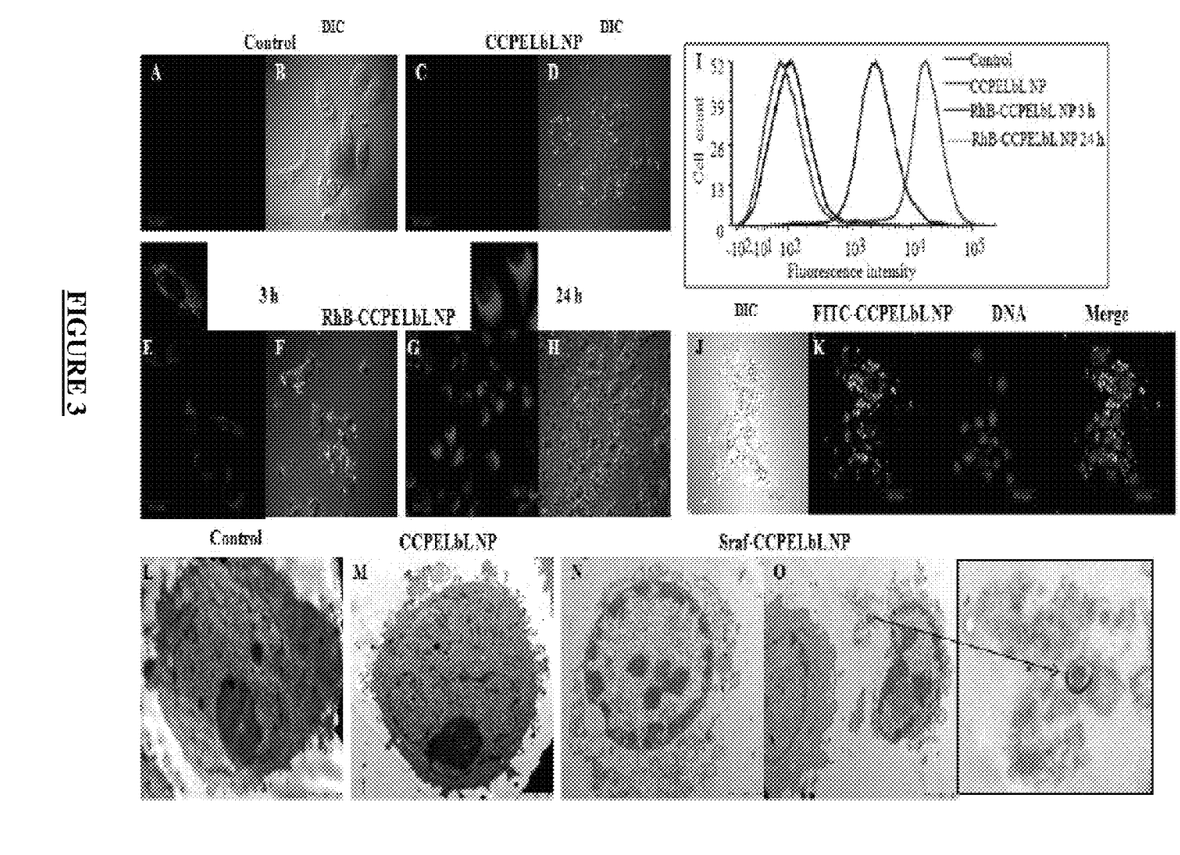

The LbL-nanoRhB (100 µg/mL) was internalized efficiently in KB cells at 3 hours and 24 hours as observed by red fluorescence in the cytoplasm (FIG. 3E-H). The control and bare CCPELbL NP (100 µg/mL) treated oral cancer cells exhibited no fluorescence signal (FIG. 3A-D). Further, a flow cytometric analysis showed that the LbL-nanoRhB exhibited a strong fluorescence signal (p<0.0001, increased cellular uptake) in KB cells at 3 hours and 24 hours (FIG. 3I) in comparison to the bare CCPELbL NP. The intracellular distribution of FITC-CCPELbL NP treated KB showed green fluorescence localized in the cytoplasm. Some of them were also localized in the cell membrane (FIG. 3J, K).

b. Transmission electron microscopic analysis: For ultra-structural studies by TEM, $1\times10^6$ cells/mL were incubated in 25 mm tissue culture flasks (Nunc, USA) with 100 µg/mL of bare CCPELbL NP and LbL-nanosoraf for 24 hours. The treated cells were centrifuged, fixed with 2.5% glutaraldehyde, washed with PBS, and then fixed with 1% osmium tetroxide. The cells were dehydrated in graded series of alcohol, embedded using DER 332-732 embedding kit (EMS, USA) and polymerized for 48 hours. These resin blocks were sectioned using an ultramicrotome (Leica Ultracut UCT, Germany). The ultrathin sections (70 nm) were transferred onto Formvar and carbon coated copper grids (EMS, USA) and processed with uranyl acetate and lead acetate solutions to visualize the cellular ultrastructures under TEM (FEI TECNAI, 12 BioTwin, Netherlands,) at 80 kV. The ultrastructural investigation by TEM was conducted to examine the intracellular fate of LbL-nanosoraf in KB cells at 24 hours. In control cells, cell membrane and nuclear morphology were found to be typical (FIG. 3L). Treatment with bare CCPELbL NP (100 µg/mL) (FIG. 3M) showed nanoparticles inside the cells with intact cell membrane and nucleus. Some of the particles were adsorbed on the cell membrane. KB cells treated with LbL-nanosoraf (100 µg/mL) (FIGS. 3N and O) exhibited a potent disrupted cell membrane with nuclear fragmentation and disturbed the nuclear envelope with serrated margins. The nuclei and cytoplasm were condensed. The insert of FIG. 3O shows that LbL-nanosoraf has been internalized by the cells (arrow). The CLSM, flow cytometric and TEM results together indicated that an efficient internalization of LbL-nanosoraf enhanced the uptake of the LbL-nanosoraf in the KB cells.

3. Anti-proliferative assay—The cytotoxicity of LbL-nanosoraf was measured by the sulfo-rhodamine B (SRB) assay. KB cells ($5\times10^4$ cells/well) were incubated in 96-well plates (Nunc, USA) for 24 hours. The cells were then treated with bare CCPELbL NP (10-250 µg/mL), free drug, Sraf (1-30 µM) and LbL-nanosoraf (1-30 µM) for 48 hours at 37° C. The absorbance was measured with a fluorescence plate reader (SPECTRAmax M2, Molecular Devices, USA) equipped with SOFTmax Pro Software (Molecular Devices) at 550 nm. The half-maximal inhibitory concentration ($IC_{50}$) was calculated using OriginPro 8.0 software. Each experiment was repeated thrice.

Figure 4:
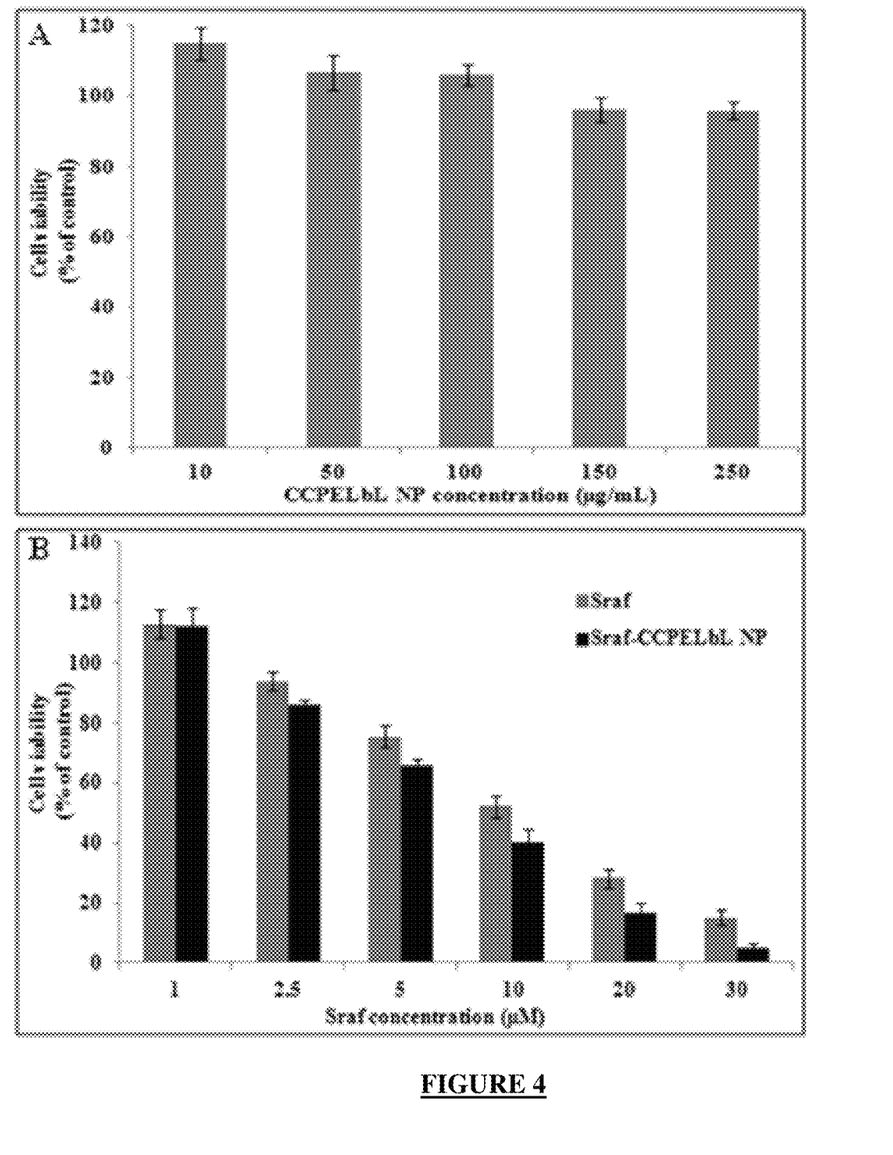
FIG. 4 depicts (A) Biocompatibility of bare CCPELbL NP, and (B) Antiproliferative activity of free drug Sraf and LbL-nanosoraf (Sraf-CCPELbL NP) at dose-dependent concentrations in KB cells after 48 hours treatment. The data represent as the mean±SD (n=3).

Sorafenib interferes with the tumor cell proliferation by inhibiting the Raf-kinase pathway. Herein the therapeutic effect of LbL-nanosoraf against oral cancer cell proliferation was evaluated by SRB assay at 48 hours. The bare CCPELbL NP (10-250 µg/mL) was non-toxic to cells, indicating its biocompatibility (FIG. 4A). KB oral cancer cells sensitivity to free drug sorafenib and LbL-nanosoraf at 1-30 µM treatments exhibited differential cytotoxicity in a dose-dependent manner at 48 hours (FIG. 4). The $IC_{50}$ of Sraf was found to be 10.6±1.8 µM whereas for LbL-nanosoraf it was 7.3±1.5 µM (FIG. 4B). The cytotoxic effect was found to be more pronounced with LbL-nanosoraf treatment than free sorafenib.

4. DNA fragmentation analysis—Apoptosis was analyzed by the DNA ladder assay. Confluent KB cells in 25 mm tissue culture flasks (Nunc, USA) were incubated with 100 µg/mL of bare CCPELbL NP, 10 µM of Sraf and 10 µM LbL-nanosoraf for 48 hours. Cells were collected, washed with PBS and lysed with (10 mmol/L Tris-HCl pH 7.4, 10 mmol/L EDTA and 0.5% Triton X-100). The lysates were incubated with 200 mg/mL Rnase A (SRL, Mumbai) for one hour followed by 200 mg/mL Proteinase K (SRL, Mumbai) for one hour at 37° C. These samples were then extracted with phenol/chloroform/isoamyl alcohol (25:24:1 v/v/v, SRL, Mumbai) followed by chloroform. DNA was precipitated in two volumes of ethanol in presence of 0.3 mol/L sodium acetate. DNA samples thus obtained were run on 2% agarose gel in TBE buffer at 50V for one hour. The bands were visualized by ethidium bromide under UV gel documentation system. The experiments were performed three times.

Figure 5:
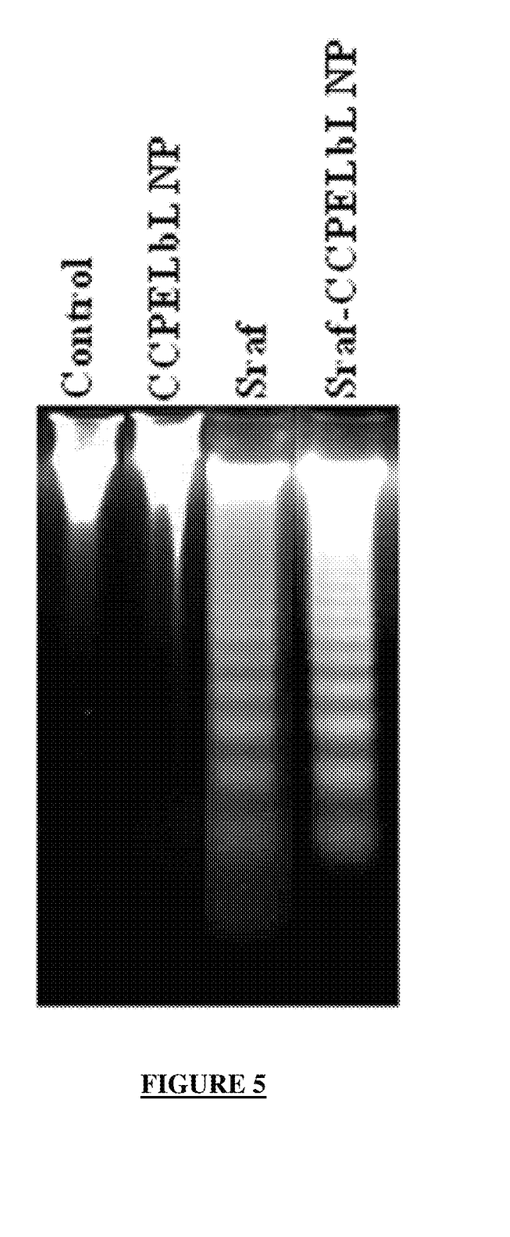
FIG. 5 illustrates DNA fragmentation analysis of free drug Sraf and LbL-nanosoraf (Sraf-CCPELbL NP) at 10 µM in KB cells at 48 hours.

Apoptosis is an intricate process involving DNA fragmentation, the hallmark for onco-chemotherapeutics. Sorafenib has been known to exhibit antiproliferative and apoptotic properties in various cancers. Therefore, the effect of LbL-nanosoraf induced an increased DNA fragmentation in KB cells than the free sorafenib at 10 μM (FIG. 5). The untreated control and bare CCPELbL NP (100 μg/mL) treated KB cells did not affect the apoptosis activity as no DNA fragments were observed. The results indicated that the potent apoptotic activity of LbL-nanosoraf was due to the strong internalization ability of LbL-nanosoraf in oral cancer cells.

5. Immunoblotting assay—Confluent KB cells plated in 25 cm² tissue culture flasks (Nunc, USA) were treated with bare CCPELbL NP (100 μg/mL), Sraf and LbL-nanosoraf at 10 μM for 48 hours at 37° C. the whole-cell lysates were collected, subjected to 10% SDS-PAGE and transferred to nitrocellulose membrane The blot was blocked in blocking buffer for one hour at room temperature and incubated with primary anti-pEGFR, anti-EGFR XP rabbit monoclonal antibodies (Cell Signaling Technology Inc., USA), anti-pERK1/2, anti-ERK1/2 rabbit monoclonal antibodies, anti-pJNK, anti-JNK rabbit polyclonal antibodies (Santa Cruz Biotechnology, USA) and anti-β-actin antibody (Cell Signaling Technology, Inc. USA) for two hours at room temperature. The bands were then visualized using secondary antibody alkaline phosphatase conjugated-antirabbit IgG (Sigma-Alrich, USA) and the immunoblots were quantified using the Image J software (National Institutes of Health, USA). The experiments were repeated three times.

Figure 6:
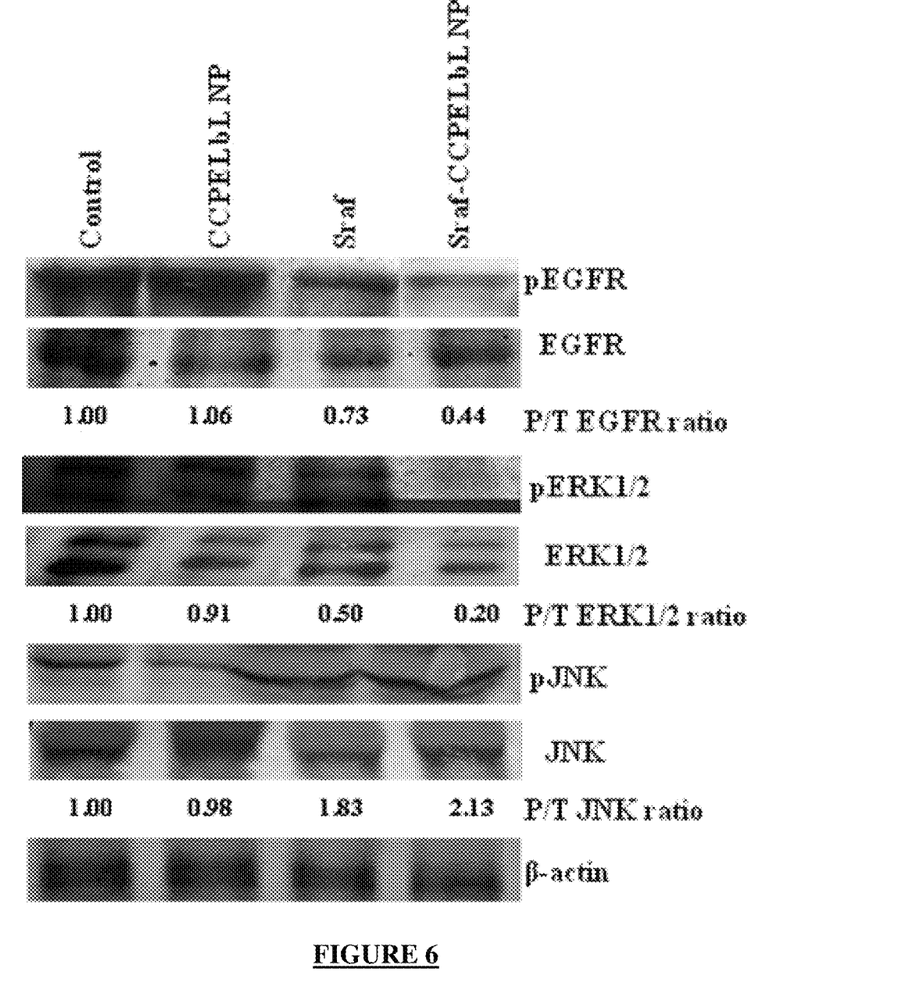
FIG. 6 depicts immunoblots showing modulatory effects on the protein expressions in KB cells at 48 hours on treatment with free drug Sraf and LbL-nanosoraf (Sraf-CCPELbL NP) at 10 µM. β-actin was used as the loading control. P/T represents phosphorylated/total EGFR, Erk1/2 and JNK ratios.

The effects of free sorafenib versus LbL-nanosoraf on protein kinase activity in KB cells were quantified by immunoblot studies. EGFR and Raf/MEK/ERK are the downstream targets of sorafenib. Hence the change in phosphorylation levels of EGFR and ERK1/2 expressions of various treatment groups in KB cells was checked by immunoblot analysis at 48 hours. Treatment with LbL-nanosoraf exhibited marked inhibition of pEGFR (P/T ratio 0.44) and pERK ½ (P/T ratio 0.20) expressions in comparison to the free sorafenib alone (P/T ratios 0.73 and 0.50 respectively) to a moderate extent at 10 μM (FIG. 6) JNK is known to be involved in cell cycle arrest and apoptosis. Sorafenib is known to be involved in JNK activation in the tumor cells thereby leading to its apoptotic effect. In this context, an analysis of LbL-nanosoraf treated cells showed a significant up-regulation of pJNK (P/T ratio 2.13) level in comparison to the free drug sorafenib (P/T ratio 1.83) at 10 μM (FIG. 6). The results indicated that the activation of JNK by LbL-nanosoraf contributes to the enhanced apoptotic effect in KB cells. In control KB cells and bare CCPELbL NP (100 μg/mL) treated cells the pEGFR, PERK1/2 and pJNK protein expression levels remained nearly unchanged. Thus the effective delivery of LbL-nanosoraf in KB cells induced potent decrease in the level of pEGFR, pERK1/2 and increase in the level of pJNK expressions, which lead to the superior anti-cancer effects.

6. Cell migration assay: Cell migration was evaluated using wound healing assay. KB cells were seeded in 6-well plates and cultured to full confluency under serum starved conditions (0.2%) for 24 hours. Wounds of one mm width were created on the monolayer with a sterile plastic 10 μL pipette tip, loose cells were washed with the medium, incubated with fresh medium treated with bare CCPELbL NP (100 μg/mL), Sraf, LbL-nanosoraf at 10 μM and observed under Nikon Inverted microscope (ECLIPSE Tiseries, Japan). Images were captured using NIS-Elements BR 4.00.00 (Build 764) imaging software after 0 hours, 4.5 hours and 9 hours of incubation at 37° C. The untreated cells and bare CCPELbL NP served as the negative controls. The migration rate of cells was expressed as the migration width in μm. Data represents the mean of three independent experiments.

Figure 7:
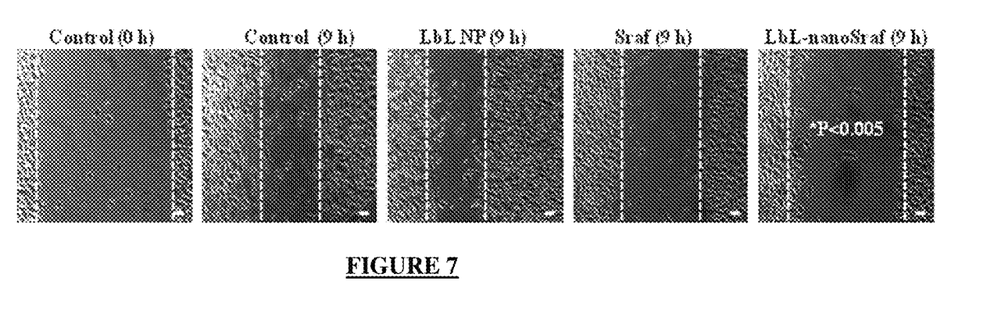
FIG. 7 shows cell migration analysis of free drug Sraf and (LbL-nanosoraf) Sraf-CCPELbL NP by wound-healing assay at 10 µM in KB cells at the end of 9 hours. Scale bar: 50 µm. The experiment was performed 3 times. *P<0.005 of LbL-nanoSraf in comparison to free Sraf.

Sorafenib is known to exhibit anti-invasive and anti-angiogenesis properties. Therefore, the anti-migratory activity of LbL-nanosoraf was evaluated by wound healing scratch assay in KB cells. The width of wound was 525±23 μm for the control in the beginning of experiment (0 h). The width of the wound was determined to be 208±28 μm and 176±32 μm in the control and bare CCPELbL NP (100 μg/mL) treated cells, respectively at 9 hours. The LbL-nanosoraf strongly blocked the migration rate of KB cells in comparison to be free 10 μM sorafenib. The width of the wound in LbL-nanosoraf and sorafenib treated KB cells at 9 hours was determined to be 454±20 μm and 303±27 μm respectively (P<0.005). Bare CCPELbL NP had no significant effect on the migration of KB cells. Sorafenib and LbL-nanosoraf retarded the migration of KB cells by 30±9% and 77±6%, respectively indicating that LbL-nanosoraf strongly blocked the migration of KB cells than sorafenib (FIG. 7). This implicated the potent anti-migratory activity of LbL-nanosoraf against oral cancer cells.

All results are expressed as the mean±standard deviation (SD). Statistical significance of the data was analyzed by one-way ANOVA using OriginPro 8.0 software. *P<0.005 was considered to be significant.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

The invention claimed is:

1. A drug delivery system for anti-cancer compounds, said system comprising
   a. a template nucleus selected from at least one of calcium carbonate, calcium phosphate and mesoporous silica for encapsulation of anti-cancer compounds,
   b. at least one anti-cancer compound is a small molecule tyrosine kinase inhibitor, its salts, solvates, analogs, polymorphs, derivatives, isomers and enantiomers thereof,
   c. at least two polyelectrolytes for polymeric layering of encapsulated anti-cancer compound, said polyelectrolytes are selected from at least one polyanionic and at least one polycationic electrolyte for forming at least two layers; one layer each of polyanionic electrolyte and polycationic electrolyte, respectively and not necessarily in that order;
   wherein said polyanionic electrolytes for polymeric layering are selected from at least one of dextran sulfate, polyethylene glycol, cellulose and alginate;

wherein said polycationic electrolytes for polymeric layering are selected from at least one of poly-L-arginine, polyglycolic acid, poly-L-lysine, chitosan and protamine;

wherein said system is a layer-by-layer nano-particulate template nucleus encapsulated anti-cancer compound.

2. The drug delivery system for anti-cancer compounds as claimed in claim 1 wherein the particle size of the system is 100-300±15 nm.

3. The drug delivery system for anti-cancer compounds as claimed in claim 1 wherein the polymeric layering of polyanionic and polycationic polymers is done in a manner that no two consecutive layers are identical.

4. The drug delivery system for anti-cancer compounds as claimed in claim 1 wherein said system is administered orally, intravenously, intratumorally or subcutaneously.

5. The drug delivery system for anti-cancer compounds as claimed in claim 1 wherein the small molecule tyrosine kinase inhibitor is selected from at least one of dasatinib, erlotinib, gefitinib, imatinib, lapatinib, nilotinib, sorafenib, sunitinib, regorafenib, vemurafenib.

6. The drug delivery system for anti-cancer compounds as claimed in claim 1 wherein said system is layer-by-layer nano-sorafenib.

7. The drug delivery system for anti-cancer compounds as claimed in claim 6, wherein the $IC_{50}$ value of layer-by-layer nano-sorafenib is about 7.3±1.5 μM.

8. The drug delivery system for anti-cancer compounds as claimed in claim 6, wherein said layer-by-layer nano-sorafenib inhibits about 77±6% of cell migration.

9. A method of preparing a drug delivery system for anti-cancer compounds, said system is a layer-by-layer nano-particulate template nucleus encapsulated anti-cancer compound comprising the steps of:
 a. adding anti-cancer compound to 0.1 M calcium chloride and mixing for ten minutes;
 b. adding solution of step a) dropwise to 0.1 M sodium carbonate solution under vigorous stirring at 2000 rpm for fifteen minutes;
 c. coating resultant calcium carbonate nanoparticles of step b) by dispersing in 5 mL of polyanionic solution containing sodium chloride; d. stirring coated nanoparticles of step c) in 5 mL of polycationic solution in 0.5M sodium chloride;
 e. repeating the coating process of c) and d) until the desired polyelectrolytes are deposited forming the multilayers;
 f. incubating the layer-by-layer nano-particulate template encapsulated anticancer compound in ethylene diamine tetraacetic acid for dissolving the template nucleus and washing the pellet carefully to remove the dissolved ions.

* * * * *